United States Patent
Wiemker et al.

(10) Patent No.: US 8,588,492 B2
(45) Date of Patent: Nov. 19, 2013

(54) VISUALIZATION OF VASCULARIZATION

(75) Inventors: Rafael Wiemker, Kosdorf (DE); Sven Kabus, Hamburg (DE); Thomas Buelow, Grosshansdorf (DE); Roland Opfer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 680 days.

(21) Appl. No.: 12/742,157

(22) PCT Filed: Nov. 4, 2008

(86) PCT No.: PCT/IB2008/054592
§ 371 (c)(1),
(2), (4) Date: May 10, 2010

(87) PCT Pub. No.: WO2009/066195
PCT Pub. Date: May 28, 2009

(65) Prior Publication Data
US 2010/0278408 A1 Nov. 4, 2010

Related U.S. Application Data

(60) Provisional application No. 60/989,134, filed on Nov. 20, 2007.

(51) Int. Cl.
*G06K 9/00* (2006.01)
*G06K 9/62* (2006.01)
(52) U.S. Cl.
USPC .............................................. 382/131; 705/2
(58) Field of Classification Search
USPC .............................................. 705/2; 382/131
See application file for complete search history.

(56) References Cited

U.S. PATENT DOCUMENTS

| 5,752,522 A * | 5/1998 | Murphy ....................... 600/587 |
| 6,609,021 B1 | 8/2003 | Fan et al. |
| 6,925,321 B2 | 8/2005 | Stefancik et al. |
| 2005/0277831 A1* | 12/2005 | Guendel ...................... 600/425 |
| 2006/0122501 A1 | 6/2006 | Lara-Montalvo et al. |

FOREIGN PATENT DOCUMENTS

| DE | 19851597 A1 | 5/1999 |
| DE | 102006002259 A1 | 7/2007 |
| WO | 03005301 A1 | 1/2003 |
| WO | 2006037217 A1 | 4/2006 |
| WO | 2007002562 A2 | 1/2007 |

OTHER PUBLICATIONS

Lee, T.-Y., et al.; CT imaging of angiogenesis; 2003; Q J Nucl. Med.; 41:171-187.
Miles, K A.; Tumour angiogenesis and its relation to contrast enhancement on computed tomography: a review; 1999; Eur. J. Radiol.; 30(3)198-205.
Shen, L., et al.; An interactive 3D visualization and manipulation tool for effective assessment of angiogenesis and ateriogenesis using computed tomographic angiography; downloaded Aug. 27, 2008. http://www.cis.umassd.edu/lshen/papers/shen_2005mi.pdf.

* cited by examiner

*Primary Examiner* — Tran Nguyen

(57) ABSTRACT

An apparatus produces image space data (35) indicative of the spatially varying strength of the vascular connections between locations in the image space and a lesion or other feature of interest. The data may be presented by way of a maximum intensity projection (MIP) display in which the brightness of the image represents the strength of the vascular connection.

19 Claims, 5 Drawing Sheets

VISUALIZATION OF VASCULARIZATION

CROSS REFERENCE TO RELATED APPLICATIONS

Figure 1:
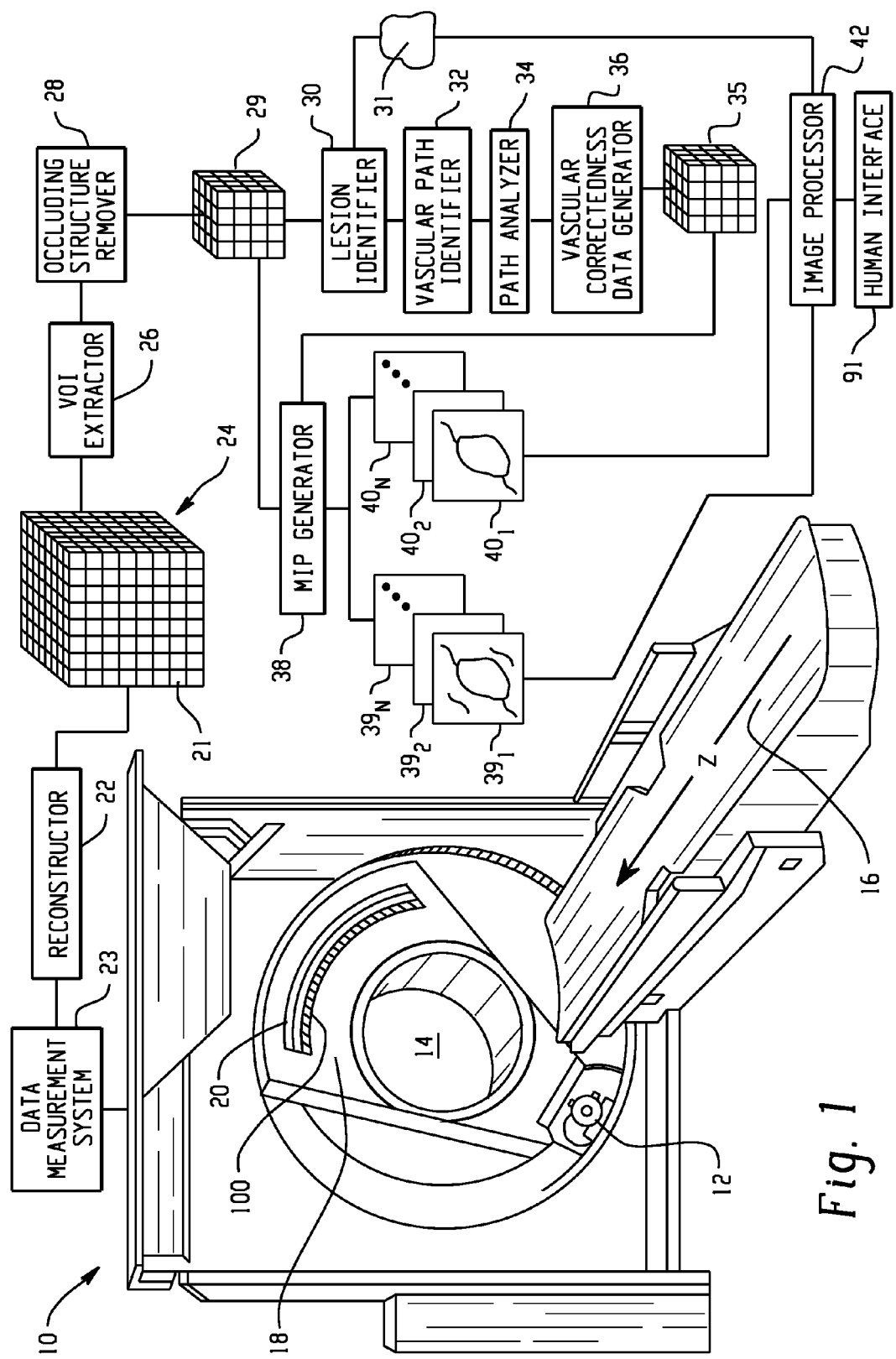

This application claims the benefit of U.S. provisional application Ser. No. 60/989,134 filed Nov. 20, 2007, which is incorporated herein by reference.

The present application relates to the visualization of vascularization. It finds particular application to visualizing the vascularization of tumors in computed tomography (CT) image data. It also relates more generally to visualizing the connectedness of other lesions or features of interest in image space data generated using other imaging modalities.

Medical imaging modalities, such as CT, magnetic resonance (MR), ultrasound (US), single photon emission computed tomography (SPECT), positron emission tomography (PET), and x-ray can play an important role in the diagnosis and treatment of diseases, such as cancer. One factor that can be used to evaluate a tumor or other suspect lesion is its vascularization. Thus, the degree and manner in which the lesion is connected to surrounding vasculature may provide useful information to the clinician, for example in connection with a determination as to whether the tumor is benign or malignant, its possible growth, and the like.

Unfortunately, vascular visualization can be complicated by a number of factors. For example, although many blood vessels may be located in the vicinity of a tumor, not all of them may contribute to the lesion blood supply. Moreover, the various blood vessels may vary in brightness and size. Smaller vessels, even if vascularly related to the tumor, may tend to be relatively less visible and have lower contrast. Larger vessels, while potentially well-visualized, may have little no or no vascular connection to the tumor.

Segmentation and related surface rendering techniques have been used to identify and present those voxels that are representative of blood vessels. Unfortunately, however, the results of the segmentation operation are generally sensitive to the segmentation algorithm and the selected segmentation parameters. For example, brightness threshold, noise suppression, and minimum thickness criteria can all influence whether a particular structure is identified as a blood vessel.

Aspects of the present invention address these matters, and others.

According to a first aspect, a method includes evaluating first image space data that includes a lesion and vasculature to determine a spatially varying strength of the vascular connections between locations in the first image space and the lesion. The method also includes generating second image space data indicative of the determined spatially-varying strength.

According to another aspect, an apparatus includes means for evaluating first image space data that includes a lesion to determine a spatially varying strength of vascular connectedness between locations in the first image space and the lesion. The apparatus also includes means for generating second, spatially-varying image space data indicative of the determined strength.

According to another aspect, a computer readable storage medium includes instructions which, when executed by a processor, cause the processor to carry out a method. The method includes evaluating first image space data that includes a feature of interest to determine a spatially-varying strength by which locations in the first image space and the feature are vascularly connected, and producing second image space data indicative of the determined spatially-varying strength.

According to another aspect, an apparatus includes means for identifying, in image space data indicative of an object, a plurality of paths that represent likely vascular connections to a lesion of the object. The apparatus also includes means for generating spatially varying vascular connectivity data representative of the likelihood that locations along the paths are vascularly connected to the lesion via the paths. Those skilled in the art will appreciate still other aspects of the present invention upon reading and understanding the attached figures and description.

FIGURES

Figure 2:
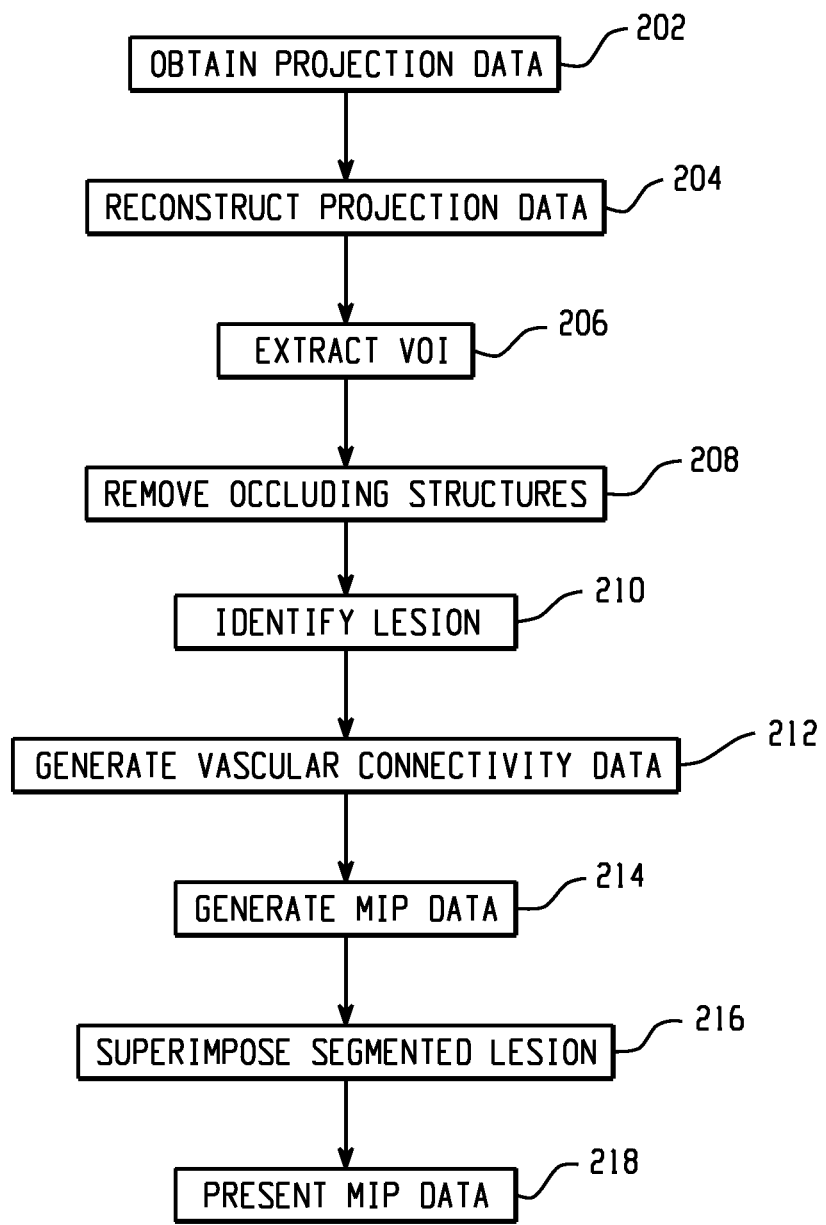

The present invention is illustrated by way of example and not limitation in the figures of the accompanying drawings, in which like references indicate similar elements and in which:

FIG. 1 depicts a CT scanner.
FIG. 2 depicts a method.
FIGS. 3A-3E depict image space data and related images.
FIG. 4 depicts a method.

With reference to FIG. 1, a CT scanner 10 includes a rotating gantry 18 that rotates about an examination region 14. The rotating gantry 18 supports an x-ray source 12, such as an x-ray tube. The gantry 18 also supports an x-ray sensitive detector 20 which subtends an arc on the opposite side of the examination region 14. X-rays produced by the x-ray source 12 traverse the examination region 14 and are detected by the detector 20. Depending on the configuration of the scanner 10 and the detector 20, the x-ray source 12 generates a generally fan, wedge, or cone shaped radiation beam that is approximately coextensive with the coverage of the detector 20. Accordingly, the scanner 10 generates projection data indicative of the radiation attenuation along a plurality of projections or rays through an object disposed in the examination region 14. A support 16, such as a couch, supports a patient or other object in the examination region 14.

A data measurement system 23 located on or near the rotating gantry 18 receives signals from the detector 20 and provides necessary analog to digital conversion, multiplexing, interface, data communication, and similar functionality.

A reconstructor 22 reconstructs the projection data acquired by the data measurement system 23 to generate image-space data 24 indicative of the interior anatomy of the patient. It will also be understood that filtering, enhancement, and/or other image processing operations may also be performed on the image space data.

Note that the foregoing is an example of one suitable CT scanner configuration and that other configurations are contemplated. In a fourth generation configuration, for example, the detector 20 generally remains stationary while the rotating gantry portion 18 rotates about the examination region. The x-ray source may be configured other than as a conventional x-ray tube; e-beam scanners which use an electron beam are also contemplated. Moreover, spectral CT system can provide information about the material composition of an object. Still other variations will be understood by those of ordinary skill in the art.

The image space data 24 is ordinarily arranged as a three-dimensional (3D) array of voxels 21. The various voxels have a value that varies as a function of a measured variable. In the case of CT image data, the measured variable is ordinarily x-ray attenuation, the value of which is conventionally expressed in Hounsfield units (HU). Thus, the voxel values would ordinarily represent the spatially varying radiation attenuation of the subject.

With ongoing reference to FIG. 1, a volume of interest (VOI) extractor 26 extracts or otherwise selects a volume or other region of interest of the image space data 24. For the purposes of the present discussion, it will be assumed that VOI selector 26 is used to select a VOI that includes a tumor, nodule, or other lesion of interest and at least a portion of the surrounding vasculature. The VOI extractor 26 may extract the VOI based on a manual input from the user, suitable automatic feature detection techniques, semi-automatically, or in another suitable fashion.

An occluding structure remover 28 may be used to remove occluding or interfering structures such as bone, neighboring tissues, and the like from the image space data to produce VOI data 29. Again, the occluding structure removal may be performed manually by the user, automatically using suitable segmentation and/or structure removal techniques, semi-automatically, or in another suitable fashion.

A lesion identifier 30 processes the image space data to identify those portions of the VOI data 29 that correspond to the lesion of interest 31. In one implementation, the lesion identifier 30 includes a segmenter that employs known segmentation techniques to segment the lesion of interest. Again, the lesion identification may be performed automatically, manually by the user, semi-automatically, or in another suitable fashion.

A vascular path identifier 32 processes the VOI data 29 to identify paths through the image space that represent possible vascular connections to the lesion. In one implementation, and as will be discussed further below, the path identifier 32 utilizes a prioritized region growing technique to preferentially identify those path(s) through the image space that are most likely to represent strong vascular connections to the lesion.

A vascular path analyzer 34 analyzes the identified paths to identify locations along the identified paths that represent relatively weak vascular connections to the lesion. More specifically, in one embodiment, the path analyzer 34 determines, for various locations in the image space, a location along the determined path between the lesion and the location that represents the weakest vascular connection.

A vascular connectedness data generator 36 generates vascular connectedness data 35 representative of the degree or strength of the vascular connection between various locations in the image space and the lesion. More specifically, the data generator 36 generates spatially varying connectedness data 35 in which the values accorded to the locations in the connectedness data 35 depend on the value of the VOI data 29 at a location determined by the path analyzer 34.

A maximum intensity projection (MIP) generator 38 operates on the VOI data 29 to generate VOI MIP data $39_{1-N}$ for one or more angles or projections through the VOI data 29. The MIP generator 38 also operates on the vascular connectedness data 36 to produce connectedness MIP data $40_{1-N}$ for corresponding projections through the vascular connectedness data 35. In the case of the VOI MIP data 39, the brightness of the various locations in the image projection represents the values encountered in the VOI data 39. In the case of the connectedness MIP data $40_{1-N}$, the values represent the strength or degree of connectedness to the lesion of interest. To facilitate the display and/or comparison of the two data sets, the voxel values may be expressed in the same units (e.g., CT numbers or HU in the case of CT data).

An image processor 42 processes the first MIP data $39_{1-N}$, the connectivity MIP data $40_{1-N}$, and the segmented lesion data 31 for presentation via a display, monitor, or other suitable human interface 91. Again to facilitate comparison, the VOI MIP data 39 and the connectivity MIP data 40 may be displayed concurrently on the interface 91, for example on a side-by-side basis. The MIP data 39, 40 may also be presented as a moving MIP display, for example by rotating the displayed MIP images in coordination about a suitable rotation axis. In one example, the images are rotated back and forth through an angle of about plus and minus ten (10) degrees to impart a sense of three-dimensionality. In another example, the MIP is rotated periodically through 360 degrees. Alternately, the user may also be afforded the opportunity to rotate the data as desired, for example via window and level, rotation, or other user operable controls.

Operation will now be described in relation to FIG. 2.

At 202, a patient is scanned to generate projection data. For the purposes of the present discussion, it will be assumed that the projection data is acquired over a region that includes at least a portion of the patient's lung. Note also that, depending on factors, such as the type of lesion, the surrounding vasculature, and the scanning modality, the scan may be coordinated with the introduction of a contrast agent to obtain contrast enhanced projection data. Such an implementation is particularly helpful where it may otherwise be difficult to differentiate some or all of the lesion or the vasculature from the surrounding tissue, as may occur when the lesion and/or vasculature are located in or near cardiac or muscle tissue.

At 204, the projection data is reconstructed to produce the image space data 24. Note also that the reconstruction 204 and succeeding operations may be performed at a time and place that is remote from the scanning operation.

At 206, a VOI is extracted from the image space data. For the purposes of the present example, it will be assumed that the VOI includes a lung lesion that is suspected of being cancerous and for which it is desirable to evaluate the blood supply to the lesion. Thus, for the purpose of the present example, the VOI would include the lesion and at least a portion of the surrounding vasculature.

Figure 3A:
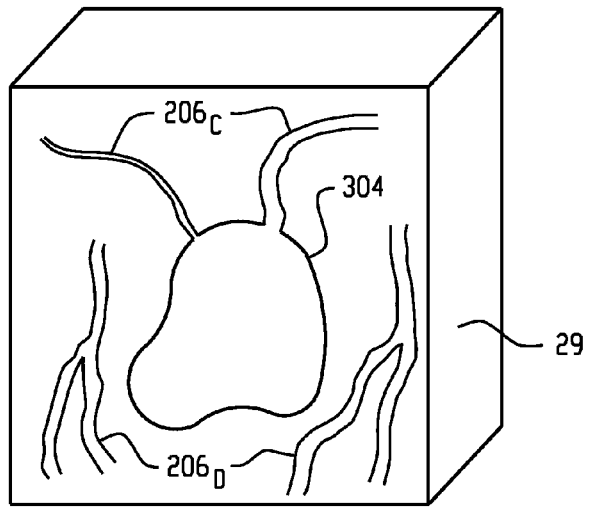
Figure 3B:
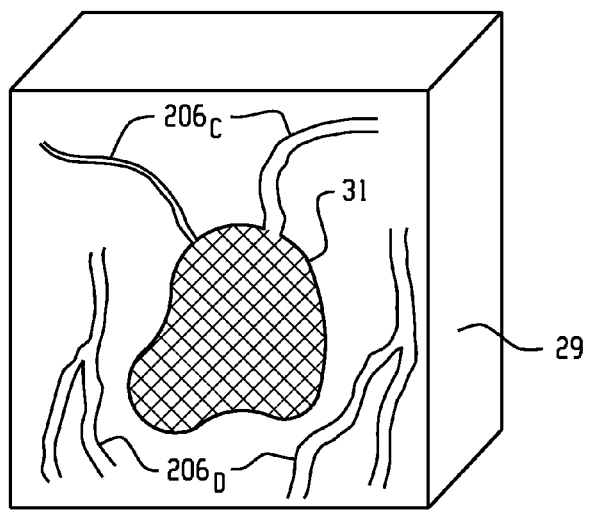
Figure 4:
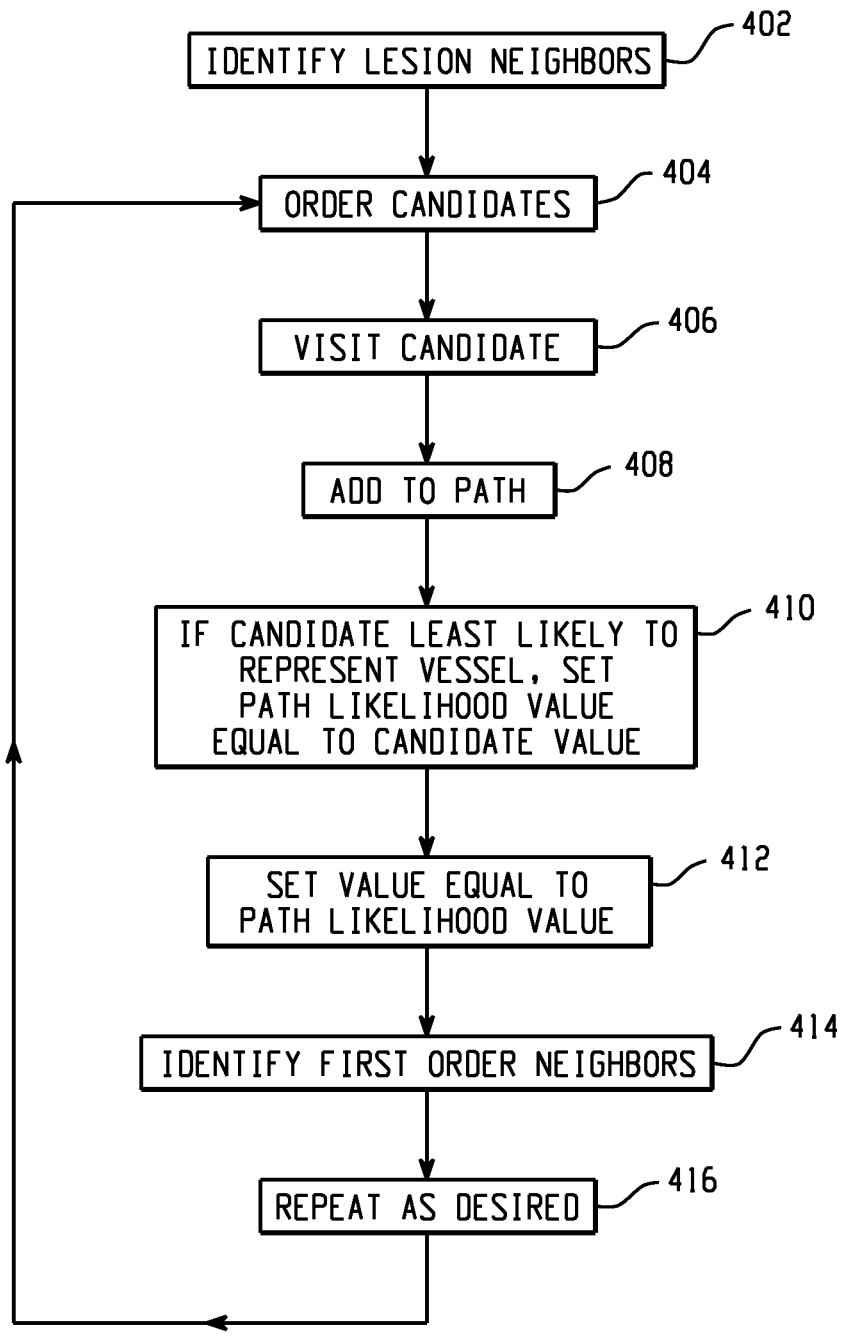

An example of an extracted VOI 29 is shown schematically in FIG. 3A. While the extracted VOI 29 is illustrated as a two-dimensional (2D) projection for ease of illustration, it will be understood that the VOI would ordinarily include a 3D volume that includes the lesion 304 and vasculature 306.

Relatively larger vessels ordinarily tend to be more visible and appear relatively brighter in the image, while relatively smaller vessels may be darker or more difficult to discern. It will also be appreciated, however, that the visibility or brightness of a vessel 306 may not necessarily correlate with the strength of this vascular connection to the lesion 304. For example, a highly visible vessel may be weakly (if at all) connected to the lesion 304, thus contributing little or nothing to the lesion 304 blood supply. On the other hand, a less visible vessel may be strongly connected to the lesion 304. For the purposes of the present example, it will be assumed that vessels $306_C$ are relatively strongly connected to the lesion 304, whereas vessels $306_D$ are weakly connected.

Occluding structures, if present in the image data, may be removed from the image data at step 208.

At 210, the lesion is identified, for example using suitable segmentation techniques. The segmented lesion 31 is illustrated generally by hatching in FIG. 3B.

Figure 3C:
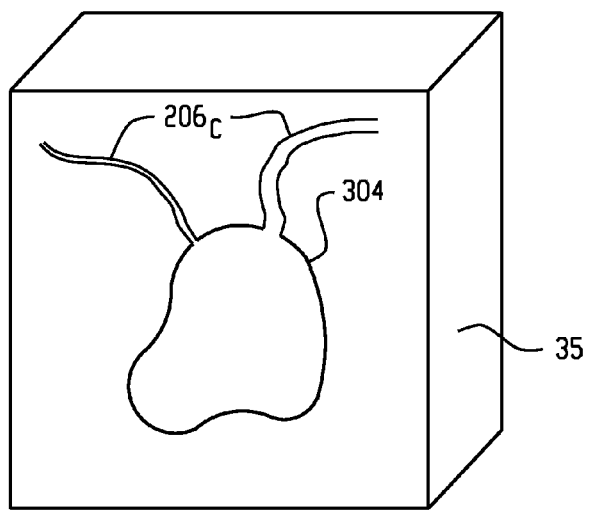
Figure 3D:
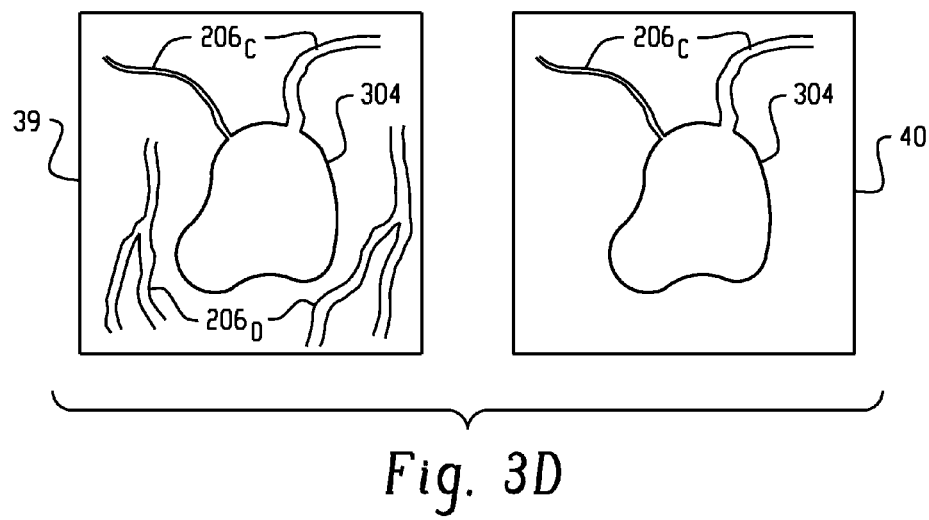
Figure 3E:
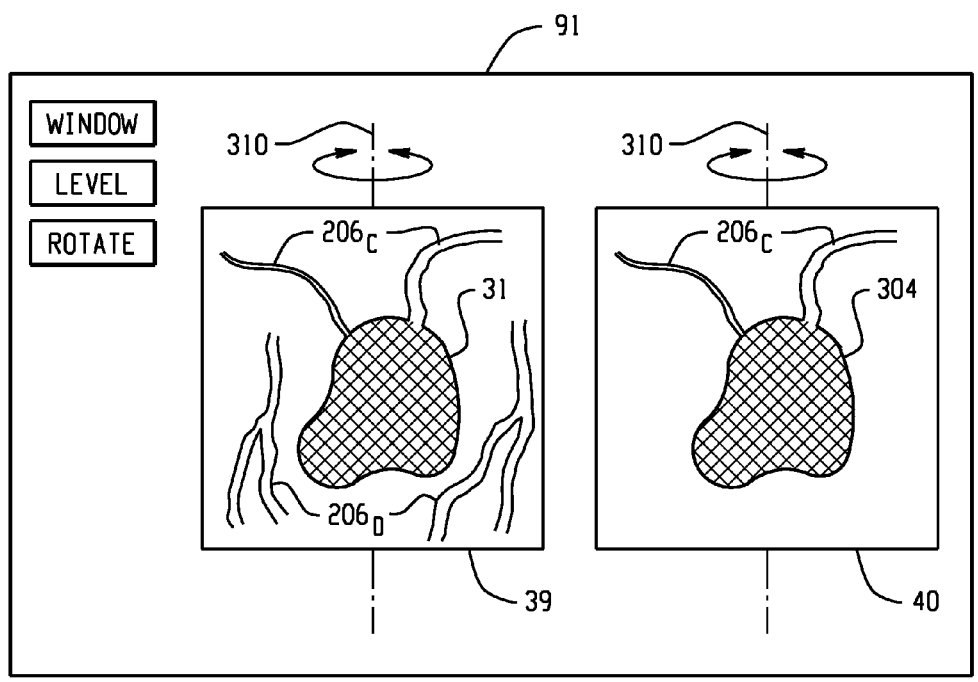

The vascular connectedness data 35 is generated at step 212, with an example of the voxel connectedness data 35 being illustrated schematically at FIG. 3C. More specifically, each location or voxel in the connectedness data 35 receives a value representative of the strength of its vascular connection to the lesion 304; each voxel in the connectedness data 35 receives a data value that is equal to the minimum voxel value encountered on the most likely vascular path between the lesion 304 and the voxel. Thus, in the present example, vessels $306_C$ are relatively "bright," whereas vessels $306_D$ are not. Stated another way, those vessels $306_D$ that are relatively less strongly connected to the lesion are suppressed.

MIP data 39, 40 is generated at step 214 for one or more projections through the connectedness data 35 and the VOI data 29, respectively. MIP data 39, 40 for an example projection is illustrated schematically at FIG. 3D.

At 216, the segmented lesion 31 may be superimposed on the MIP data 39, 40.

The MIP data 39, 40 is presented to the user at step 218. In one implementation illustrated schematically in FIG. 3E, MIP data 39, 40 for corresponding projections though the image space is presented side-by-side via the human interface 91. As noted above, a moving MIP display may be generated rotating the presented projections about a suitable axis of rotation 310.

Generation of the vascular connectedness data 35 will now be further described with reference to FIG. 4, which illustrates an example prioritized region growing technique in which the brightness of the voxels in the connectedness data 35 represents the minimum brightness of the voxels located along the strongest vascular path between the lesion and the voxel.

At 402, those voxels that border on the lesion (i.e., its first order neighbors) are identified and considered candidate voxels.

At 404, the candidate voxels are ordered according to the likelihood that they represent a blood vessel.

Note that various likelihood criteria may be used. According to one technique, the candidate voxels are ordered according to their relative data values, for example with the relatively higher values being considered first. Such a technique is particularly useful in situations, such as the CT imaging of lung lesions where voxels representative of blood vessels are relatively contrasty compared to surrounding tissues. In a variation, only those voxels within a certain range may be considered, with the voxels ordered according to their location in the range. Additionally or alternatively, morphological or other information may be used. Those of ordinary skill in the art will recognize that the above are only examples and that other variations may be employed as appropriate. Moreover, path generation techniques other than region growing may be employed.

At 406, the candidate voxel that is most likely to represent a blood vessel is visited.

At 408, the visited voxel is added to a path. Note that, depending on the likelihood that the visited voxel represents a blood vessel and the location of the visited voxel, the visited voxel may be added to an already existing path, considered to be a branch of an existing path, or form the start of a new path.

At 410, if the visited voxel is the least likely of the voxels along the current path to represent a connection to the lesion, a path likelihood value for the current path is set to the value of the visited voxel. In the case of CT data in which the VOI data 29 is expressed in HU, the path likelihood value may likewise be expressed in HU.

At 412, the voxel in the connectedness data 35 having a location that corresponds to the location of the visited voxel is set to the current path likelihood value.

At 414, the first order neighbors of the visited voxel are identified.

At 416, the process is repeated as desired, for example until all voxels of the first image space 29 have been visited.

One advantage of the techniques as described above is that the degree of connectedness may be represented by the relative brightness of the vessel. Moreover, the visualization process does not rely on an implicit binary determination as to whether a particular vessel is connected to the tumor. Relative to surface renderings, MIP projections in general also do not require brightness thresholds, are relatively less prone to the suppression of fainter structures, and tend to be more robust with respect to image noise.

It will also be understood that the order of the various steps may be varied. For example, the analysis of the least likely vascular connection along a given path need not be conducted contemporaneously with the generation of the path and may be performed in a separate step. Breadth first, depth first, and other ordering techniques may be employed. The paths may also be identified using other than region growing.

Still other variations are contemplated. For example, the above-described techniques are not limited to CT data and may be employed in connection with image data generated using other modalities, including but not limited to MR, US, SPECT, PET, and x-ray. They may also be employed in connection with lesions others than tumors and nodules, and also to visualize connectedness to structures other than lesions. They may also be employed to visualize connectedness other than vascular connectedness.

Various display and visualization techniques are also contemplated. As one example, the connectedness data 35 may also be presented using volume rendering techniques. As still another example, the connectedness brightness value may be expressed by way of changes in color or shading.

It will be appreciated that various of the techniques above may be implemented via varying combinations of hardware and/or computer software or firmware. In the case of software, firmware, or the like, computer readable instructions may be stored on a computer readable storage medium. When executed by a computer processor, the instructions cause the processor to carry out the described techniques. The instructions may also be located remotely and accessed as required, for example by downloading them via the internet.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method comprising:
   evaluating, with a processor, first image space data that includes a lesion and vasculature to determine a spatially varying strength of the vascular connections between locations in the first image space and the lesion;
   identifying, with the processor, in the first image space data, a first path that represents a vascular connection to the lesion, wherein the path includes a first location;
   identifying, with the processor, a second location along the path that satisfies a predetermined connection strength threshold between the first location and the lesion; and
   generating, with the processor, second image space data indicative of the determined spatially-varying strength.

2. The method of claim 1 including presenting an image indicative of the second image space data, wherein the presented image includes a spatially-varying characteristic that is indicative of the determined spatially-varying strength.

3. The method of claim 2 wherein the characteristic includes a brightness.

4. The method of claim 1 wherein the first image data is indicative of an object and the method includes setting the value of a location in the second image space data that corresponds to the first location to a value indicative of a measured characteristic of the object at the second location.

5. The method of claim 4 wherein the characteristic includes an x-ray attenuation.

6. The method of claim 1 including generating MIP data indicative of the second image space data.

7. The method of claim 6 including:
generating MIP data indicative of the first image space data;
concurrently presenting the MIP data indicative of the first image space data and the MIP data indicative of the second image space data in a human perceptible form.

8. The method of claim 1 wherein the first path represents the strongest vascular connection between the first location and the lesion and the second location represents the weakest vascular connection along the first path.

9. The method of claim 1 including:
extracting the first image space data from third image space data indicative of an object, wherein the image space data includes the lesion and at least a portion of the surrounding vasculature;
segmenting the lesion;
presenting an image indicative of the segmented lesion and the second image space data.

10. An apparatus comprising:
a computer processor that evaluates first image space data that includes a lesion to determine a spatially varying strength of vascular connectedness between locations in the first image space and the lesion; wherein the computer processor identifies in the first image space data, a first path that represents a vascular connection to the lesion, wherein the path includes a first location; wherein the computer processor further identifies a second location along the path that satisfies a predetermined connection strength threshold between the first location and the lesion; wherein the computer processor generates second, spatially-varying image space data indicative of the determined strength.

11. The apparatus of claim 10 comprising an imaging apparatus that generates the first image space data.

12. The apparatus of claim 10 including:
an occluding structure remover;
a lesion identifier;
a vascular path generator;
a vascular path analyzer; and
a vascular connectedness data generator.

13. A non-transitory computer readable storage medium including instructions which, when executed by a processor, cause the processor to carry out a method that includes:
evaluating first image space data that includes a feature of interest to determine a spatially-varying strength by which locations in the first image space and the feature are vascularly connected;
identifying a vascular path through the first image space;
identifying a location along the path that satisfies a predetermined connection strength threshold;
using first image space data at the identified location to produce the second image space data indicative of the determined spatially-varying strength.

14. The computer readable storage medium of claim 13 wherein the first image space data is indicative of an object and the method includes:
using a region growing technique to identify a vascular path between the feature and a first location;
identifying a second location along the path that represents the weakest vascular location between the feature and the first location;
setting a location in the second image space data to a value representative of a measured characteristic of the object at the second location.

15. The computer readable storage medium of claim 14 wherein the characteristic is measured by an MR scanner, a PET scanner, or a SPECT scanner.

16. The computer readable storage medium of claim 13 wherein the method includes:
presenting an image indicative of the second image space data, wherein the image includes a spatially-varying brightness that represents the spatially-varying strength.

17. The computer readable storage medium of claim 13 wherein the method includes generating MIP data indicative of the second image space data.

18. The computer readable storage medium of claim 13 wherein the method includes:
identifying the feature of interest;
identifying first locations that neighbor the feature of interest;
ordering the identified locations according to the likelihood that the identified locations represent a vascular path;
identifying second locations that neighbor the identified first location that represents the most likely vascular path;
repeating the steps of ordering and identifying second locations.

19. An apparatus comprising:
a computer processor that identifies, in image space data indicative of an object, a plurality of paths that represent vascular connections to a lesion of the object;
identifying a first vascular path from the plurality of paths;
identifying a location along the first vascular path that satisfies a predetermined connection strength threshold; wherein the computer processor generates spatially varying vascular connectivity data representative of the likelihood that a location along the first vascular path are vascularly connected to the lesion via the first vascular path.

* * * * *